United States Patent
Yeole et al.

(10) Patent No.: US 9,809,832 B2
(45) Date of Patent: Nov. 7, 2017

(54) MICROBIAL BIOTRANSFORMATION OF AROMATIC ACIDS TO THEIR REDUCED CARBON AROMATIC ACIDS

(71) Applicant: PRIVI BIOTECHNOLOGIES PRIVATE LIMITED, Mumbai, Maharashtra (IN)

(72) Inventors: Mahendra M Yeole, Mumbai (IN); Aparna Gala, Mumbai (IN); Arvind M. Lali, Mumbai (IN)

(73) Assignee: PRIVI BIOTECHNOLOGIES PRIVATE LIMITED, Navi Mumbai, Maharashtra (IN)

( * ) Notice: Subject to any disclaimer, the term of this patent is extended or adjusted under 35 U.S.C. 154(b) by 186 days.

(21) Appl. No.: 14/424,634

(22) PCT Filed: Aug. 28, 2013

(86) PCT No.: PCT/IN2013/000525
§ 371 (c)(1),
(2) Date: Feb. 27, 2015

(87) PCT Pub. No.: WO2014/045298
PCT Pub. Date: Mar. 27, 2014

(65) Prior Publication Data
US 2015/0211029 A1    Jul. 30, 2015

(30) Foreign Application Priority Data
Aug. 28, 2012    (IN) .......................... 2496/MUM/2012

(51) Int. Cl.
C12P 7/40    (2006.01)
C12P 7/42    (2006.01)

(52) U.S. Cl.
CPC ..................... C12P 7/42 (2013.01)

(58) Field of Classification Search
None
See application file for complete search history.

(56) References Cited

U.S. PATENT DOCUMENTS 5,278,064 A * 1/1994 Berry ......................... C12P 1/06
424/122
5,350,579 A * 9/1994 Berry ......................... C12P 1/06
424/122
6,133,003 A * 10/2000 Rabenhorst ............... C12P 7/24
426/44
2004/0203123 A1* 10/2004 Rabenhorst ............ C12N 15/74
435/147
2013/0115667 A1    5/2013 Zheng et al.

FOREIGN PATENT DOCUMENTS

EP    2157184 A1    2/2010

OTHER PUBLICATIONS

Achterholt et al. Appl Microbiol Biotechnol (2000) 54: 799-807.*
Grund et al., "Catabolism of Benzoate and Monohydroxylated Benzoates by *Amycolatopsis* and *Streptomyces* spp.," Applied and Environmental Microbiology, vol. 56, No. 5, pp. 1459-1464, May 1990.
Max et al., "Decarboxylation of Ferulic Acid to 4-Vinyl Guaiacol by *Streptomyces setonii*," Applied Biochemistry and Biotechnology, vol. 66, pp. 289-299, 2012.
Fleige et al."Investigation of the *Amycolatopsis* sp. Strain ATCC 39116 Vanillin Dehydrogenase and its Impact on the Biotechnical Production of Vanillin," Applied Environmental and Microbiology, vol. 79, No. 1, pp. 81-90, 2013.
Sutherland et al., "Metabolism of cinnamic,p -coumaric, and ferulic acids by *Streptomyces setoni*," Canadian Journal of Microbiology, vol. 29, No. 10, pp. 1253-1257, 1983.
Muheim et al., "Towards a high-yield bioconversion of ferulic acid to vanillin," Applied Microbiology and Biotechnology, vol. 51, pp. 456-461, 1999.
Karegoudar et al., "Microbial Degradation of Monohydroxybenzoic Acids," The Journal of Microbiology, vol. 38, No. 2, pp. 53-61, 2000.
Davis et al., Genome Sequence of *Amycolatopsis* sp. Strain ATCC 39116, a Plant Biomass-Degrading Actinomycete, Journal of Bacteriology, vol. 194, No. 9, pp. 2396-2397, May 2012.

* cited by examiner

Primary Examiner — Chris R Tate
Assistant Examiner — Douglas F White
(74) Attorney, Agent, or Firm — Drinker Biddle & Reath LLP

(57) ABSTRACT

The present invention relates to a method for microbial fermentation and biotransformation of aromatic acids to aromatic acids with reduced carbon atoms of wide commercial importance using a culture of actinomycete species. *Amycolatopsis* sp or the mutant thereof is employed in the present invention to convert natural as well as synthetic aromatic acids to reduced carbon aromatic acids with wide applications. The said culture in the disclosed invention is adapted to grow at 37-46° C. to achieve the biotransformation of aromatic acid to reduced carbon aromatic acid is accomplished at 37-46° C. to obtain a higher yield of the product.

21 Claims, 1 Drawing Sheet

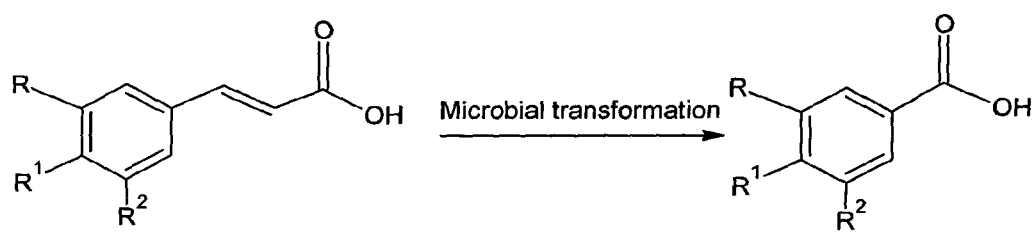

MICROBIAL BIOTRANSFORMATION OF AROMATIC ACIDS TO THEIR REDUCED CARBON AROMATIC ACIDS

TECHNICAL FIELD OF INVENTION

The present invention relates to a method for microbial fermentation and biotransformation of aromatic acids to aromatic acids with reduced carbon atoms of wide commercial importance using a culture of actinomycete species.

BACKGROUND OF THE INVENTION

The biodegradation of phenyl propanoids is important for the global carbon cycle from an environmental point of view, since these compounds are released from plant wastes as breakdown products from lignin. With the improvement of living conditions, demand for natural or green products has increased. In contrast to chemical synthesis, biological methods have the advantages such as mild reaction condition, fewer byproducts, less environmental pollution, selectivity and simpler downstream processing. However, in most reported cases, the transformation yields are very low and only a few of them are cost effective for commercial production. Much scientific interest has been focused on the ability of micro organisms to metabolize the hydroxy cinnamic acids such as ferulic acid, p-coumaric acid, caffeic acid, sinapic acid into hydroxy benzoate derivatives which are of commercial importance.

Para-hydroxy benzoic acid and its derivatives are widely used as preservatives by cosmetic and pharmaceutical industries. For example para-hydroxy benzoic acid is effective preservatives in many types of formulas. These compounds, and their salts, are used primarily for their bactericidal and fungicidal properties. They can be found in shampoos, commercial moisturizers, shaving gels, personal lubricants, topical/parenteral pharmaceuticals, spray tanning solution, makeup, and toothpaste. They are also used as food additives.

Cultures of *S. sannanensis* when grown on minimal medium containing ferulic acid as sole carbon source, vanillic acid accumulation was observed in the medium as the major biotransformed product along with transient formation of vanillin. A maximum amount of 400 mg/L vanillic acid accumulation was observed, when cultures were grown on 5 mM ferulic acid at 28° C. This accumulation of vanillic acid was found to be stable in the culture media for a long period of time, thus facilitating its recovery (*Microbial transformation of ferulic acid to vanillic acid by Streptomyces sannanensis MTCC 6637 J Ind Microbiol Biotechnol* (2007) 34:131-138)

*Sporotrichum thermophile* is capable of promoting the formation of vanillic acid during ferulic acid degradation. Ferulic acid metabolism by *S. thermophile* apparently occurred via the propenoic chain degradation and the formation of 4-hydroxy-3-methoxystyrene (4-vinylguaiacol) was observed which was presumably metabolized to vanillic acid. (*Bioconversion of ferulic acid into vanillic acid by the thermophilic fungus Sporotrichum thermophile Lebensm.- Wiss. u.-Technol.* 36 (2003) 561-565). Guaiacol was detected in addition to the above-mentioned intermediates, usually as a result of nonoxidative decarboxylation of vanillic acid. Under optimum conditions vanillic acid production from ferulic acid by *S. thermophile* attained very high levels of 4798 mg/L with a molar yield of 35%.

Biotransformations of cinnamic and ferulic acidl catalyzed by actinomycetes have been studied. Strain GE 107678, identified as *Streptomyces halstedii*, converted cinnamic acid in cinnamamide (95% molar conversion from 2 g/L of substrate) and ferulic acid in vanillic acid (80% molar conversion from 1 g/L of substrate) with transient formation of low amounts of vanillin (0.10-0.15 g/L). Strain GE 107678 resulted the most promising, since it was able to convert cinnamic acid into the corresponding amide with high yield (*Biotransformations of cinnamic and ferulic acid with actinomycetes Enzyme and Microbial Technology* 34 (2004) 3-9).

The enzymatic formation of p-hydroxybenzoic acid from p-coumaric acid has been detected in cell free extracts of *Lithospermum erythrorhizon* cell cultures. In the absence of NAD, p-hydroxybenzaldehyde is formed instead of p-hydroxybenzoic acid. The reaction is specific to p-coumaric acid. In addition, a p-hydroxybenzaldehyde dehydrogenase activity is also found. The results suggest that the reaction mechanism is non-oxidative (*Formation of p-hydroxy benzoic acid from p-coumaric acid by cell free extract of Lithospermum erythrorhizon cell cultures Phytochemistry*, Volume 30, Issue 7, 1991, Pages 2233-2236).

Cell suspensions of *Acinetobacter calcoaceticus* strain DSM 586 and DSM 590 were able to grow on benzoic, p-hydroxybenzoic and vanillic acid as sole carbon source. Cells induced with trans-ferulic acid were able to oxidize trans-ferulic, p-coumaric, vanillic, p-hydroxybenzoic and protocatechuic acid at rates higher than the uninduced culture. The same activity was found in the p-coumaric acid induced culture. Two aromatic compounds, vanillic and p-hydroxybenzoic acid, were isolated from culture filtrates of trans-ferulic and p-coumaric acid grown cells, respectively (*Degradation of trans-ferulic acid and p-coumaric acid. Biochim Biophys Acta.* 1995 Jun. 9; 1244 (2-3):363-7).

*Streptomyces setonii* strain 75Vi2 was grown at 45° C. in liquid media containing yeast extract and trans-cinnamic acid, p-coumaric acid, ferulic acid, or vanillin. Cinnamic acid was catabolized via benzaldehyde, benzoic acid, and catechol; p-coumaric acid was catabolized via p-hydroxybenzaldehyde, p-hydroxybenzoic acid, and protocatechuic acid; ferulic acid was catabolized via vanillin, vanillic acid, and protocatechuic acid. When vanillin was used as the initial growth substrate, it was catabolized via vanillic acid, guaiacol, and catechol (*Can J Microbiol.* 1983 October; 29(10:1253-7).

U.S. Pat. No. 6,844,019 discloses use of *Pseudomonas putida* to convert ferulic acid to vanillic acid, wherein the process of the invention converted 28.5 g/L ferulic acid to 19.05 g/L of vanillic acid with an overall yield of 91.48% and a conversion rate of 84.38% after 160 hrs by fed batch method.

Another U.S. Pat. No. 6,844,019 discloses the use of *Rhodotorula glutens* to convert p-coumaric acid to p-hydroxy benzoic acid. 2.1 g/L of p-hydroxy benzoic acid was obtained from 4 g/L of p-coumaric acid. 3,4-dihydroxybenzoic acid was also obtained as byproduct in the concentration of 0.47 g/L. The process was gave 62.39% yield and 97% conversion.

U.S. Pat. No. 5,866,380 employs *Aspergillus niger* MIC 373, wherein ferulic acid was added in continuous fashion in doses of 0.430 g/L per 24 hrs. After 15 days, 5.05 g/L ferulic acid was consumed, 3.6 g/L vanillic acid and 0.109 g/L MHQ was produced. Yield of vanillic acid was 82%.

Another U.S. Pat. No. 5,866,380 also employs the *Actinomycete streptomyces setonii* ATCC 25497, wherein ferulic acid was added in the concentration of 1 g/L. After 100 hrs, 0.88 g/L ferulic acid was consumed, and 0.332 g/L vanillic acid was produced. Molar yield of vanillic acid was 43%.

US20060292676 employs *Aspergillus niger* CGMCC 0774 to convert ferulic acid to vanillic acid. A solution of rice bran oil was added in proportion of 10g/ 100 ml of culture. The concentration of ferulic acid in the culture was 2.02g/100 ml, was subjected to hydrolysis by fermentation at temperature of 37° C. for 24 hrs. The final concentration of ferulic acid and that of vanillic acid was 1.22 g/100ml and 0.68 g/100 ml respectively.

SUMMARY OF THE INVENTION

One object of the present invention is to provide a process for microbial fermentation and biotransformation of aromatic acids to selective aromatic acids with reduced carbon atoms without affecting other functional groups using a culture of actinomycete species.

Another object of the invention is to provide a process for biotransformation of natural and/or synthetic aromatic acids like substituted phenyl propenic acids, wherein substituted groups, R, R1, R2 may be hydrogen and/or amino and/or hydroxyl and/or alkoxy group and/or any other substitutions and all the similar substrates which are aromatic acids with propenic acid side chain and with different substituent at various positions on the aromatic ring.

Yet another objective of present invention is to provide a process for the biotransformation of the aromatic acid precursor, wherein the initial substrate concentration is maintained in the biotransformation medium, thereby showing a high tolerance of the organism for the substrate resulting in a higher conversion rate of the substrate.

Another object of the invention is to provide a process with increasing in the productivity of reduced carbon aromatic acid and simplifying the downstream processing of the product.

Another object of the present invention is to provide a process for recovery and recycling of cells in the continuous manner and multiple cycles of the biotransformation resulting in cost effective as it saves the media cost and the time and energy for the growth of the organism.

Yet another object of the present invention is to provide a process for microbial production of reduced carbon aromatic acid from aromatic acid with mild reaction condition and environmentally benign.

BRIEF DESCRIPTION OF THE DRAWING

FIG. 1: is a view illustrating the process for biotransformation of natural and/or synthetic aromatic acids, e.g. substituted phenyl propenic acids, wherein the substituted groups, R, R1, R2 may be hydrogen and/or amino and/or hydroxyl and/or alkoxy group and/or any other substitutions and all the similar substrates which are aromatic acids with propenic acid side chain and with different substituent at various positions on the aromatic ring.

DETAILED DESCRIPTION OF THE INVENTION

The present invention relates to a process in which microbes are employed to produce industrially useful reduced carbon aromatic acids which are pharma intermediates, food additives, flavors etc from naturally occurring as well as synthetic aromatic acids. The reaction conditions employed in the disclosed method are mild and environmentally benign. The present invention also discloses an effective process for the selective production of aromatic acids with reduced carbon atoms without affecting other functional groups on the aromatic ring using the organism of Actinomycete species, *Amycolatopsis mediterranei*.

One of the aspects of the present invention is to provide a process for microbial fermentation and biotransformation of aromatic acids to selective aromatic acids with reduced carbon atoms without affecting other functional groups using a culture of actinomycete species, *Amycolatopsis mediterranei*, wherein the process comprises culturing or growing the microbial, *Amycolatopsis* cells on sole carbon source such as glucose and/or starch and/or molasses and/or sugar hydrolyzate from wood and other lignocelluloses biomass. In this process, the substrates in growth medium are not used as a carbon source and/or as inducer for the organism and therefore all the substrate is directed towards product formation without affecting the product yield.

Another aspect of the present invention is to provide a process for the biotransformation of aromatic acids to their reduced carbon aromatic acids, wherein the process comprises: culturing or growing *Amycolatopsis mediterranei* NCIM 5008 in a fermentor at a temperature in the range of 37-46° C. for 16-24 hours; adding the alkaline solution of substrate containing aromatic acid to the fermentation broth to obtain the final concentration of 1-15 g/L for aromatic acid; wherein aromatic acid is converted for 24-50 hours and converted liquid containing reduced carbon aromatic acid is obtained; centrifuging or filtrating the converted liquid to obtain retentate comprising culture cells, and permeate comprising converted liquid with reduced carbon aromatic acid; precipitating the converted liquid obtained from above step to isolate crude reduced carbon aromatic acid in solid form; and recrystallizing the crude reduced carbon aromatic acid to obtain pure reduced carbon aromatic acid.

One of the embodiment of the present invention there is provided a process for biotransformation of natural and/or synthetic aromatic acids, wherein the said process comprising: culturing or growing *Amycolatopsis mediterranei* NCIM 5008 in a fermentor at a temperature in the range of 37-46° C. for 16-24 hours; adding the alkaline solution of substrate containing aromatic acid to the fermentation broth to obtain the final concentration of 1-15 g/L for aromatic acid; wherein aromatic acid is converted for 24-50 hours and converted liquid containing reduced carbon aromatic acid is obtained; centrifuging or filtrating the converted liquid to obtain retentate comprising culture cells, and permeate comprising converted liquid with reduced carbon aromatic acid; precipitating the converted liquid obtained from above step to isolate crude reduced carbon aromatic acid in solid form; and recrystallizing the crude reduced carbon aromatic acid to obtain pure reduced carbon aromatic acid.

Another embodiment of the present invention there is provided a process for biotransformation of natural and/or synthetic aromatic acids to its reduced carbon aromatic acid, wherein said natural and/or synthetic acid is selected from the group consisting of cinnamic acid, 3-methoxy-4-hydroxy cinnamic acid, 4-hydroxy cinnamic acid, 3-hydroxy cinnamic acid, caffeic acid, sinapinic acid, hydrolyzate of lignin, hydrolyzate of phenolate acid, most preferably 3-methoxy-4-hydroxy cinnamic acid or caffeic acid or p-coumaric acid.

Another embodiment of invention there is provided a process for biotransformation of natural and/or synthetic aromatic acids to reduced carbon aromatic acids, wherein said reduced carbon aromatic acid is selected from the group consisting of benzoic acid, 4-hydroxy-3-methoxy benzoic acid, 4-Hydroxy benzoic acid, 3-hydroxy benzoic acid, 3,4-dihydroxy benzoic acid, 3,5-dimethoxy-4-hydroxy benzoic acid, most preferably 4-hydroxy-3-methoxy benzoic acid or protocatechuic acid or p-hydroxy benzoic acid.

In one of the most preferred embodiment of the present invention there is provided a process for biotransformation of natural and/or synthetic aromatic acids like substituted phenyl propenic acids, wherein substituted groups R, R1, R2 may be hydrogen and/or amino and/or hydroxyl and/or alkoxy group and/or any other substitutions and all the similar substrates which are aromatic acids with propenic acid side chain and with different substituent at various positions on the aromatic ring.

In yet another embodiment of the present invention, wherein the described process is not limited to the above mentioned aromatic acids but can be applied to other similar aromatic acids with different substituents but similar propenic acid side chain.

Another embodiment of the present invention, wherein the culture may only reduce the propenic side chain without affecting other substituent at different positions like amino, hydroxyl, methoxy groups or any other substitutions.

Another embodiment of the present invention, wherein aromatic acid substrates used for biotransformation may be aromatic acids with propenic acid side chain and with different substituents as shown in FIG. 1.

The other embodiment of the present invention the growth of cell culture by the microorganism may be carried out on a carbon and nitrogen source, wherein carbon source is selected from the group consisting of glucose, molasses, starch, sugar hydrolyzate, corn steep liquor, most preferably glucose.

In other embodiment of the present invention, wherein glucose used may be in the concentration range from 1-40 g/L, more preferably in the range of 5-20 g/L.

Another embodiment of the present invention the nitrogen source used may be organic and/or inorganic source, wherein organic source is selected from the group consisting of yeast extract, malt extract, peptone, beef extract, soy protein extract, maize gluten protein extract and/or inorganic source is selected from the group consisting of ammonium sulphate, urea, and sodium nitrate.

In another embodiment of the present invention, wherein nitrogen source used may be in the range of concentration of 5-50 g/L, most preferably in the range of 5-20 g/L.

The other embodiment of the present invention, wherein substrate concentration used for biotransformation may be in the range of 1-20 g/L, more preferably 5-12 g/L.

In yet another embodiment of the present invention, wherein alkaline pH of the substrate solution may be adjusted in the range of 6-9, more preferably 8-9.

In another embodiment of the present invention, wherein pH of the growth media may be formulated in the range of 6-9, most preferably 7-8.5.

The other embodiment of the present invention, wherein an addition of substrate solution may be done in one step or step-wise manner.

Another embodiment of the present invention, wherein conversion of aromatic acid to their reduced carbon aromatic acid may be carried out within 30-40 hours at a temperature in the range of 39 to 45° C. in a fermentation broth.

Another embodiment of the present invention, wherein aromatic acid substrates in growth medium may be not used as a carbon source and/or as inducer for its growth and metabolism by the organism.

In most preferred embodiment of the present invention the biotransformation of natural and/or synthetic aromatic acids may be carried out to reduced carbon aromatic acid, wherein natural and/or synthetic aromatic acids are substituted phenyl propenic acids, wherein substituted groups, R, R1, R2 may be hydrogen and/or amino and/or hydroxyl and/or alkoxy group and/or any other substitutions and all the similar substrates which are aromatic acids with propenic acid side chain and with different substituent at various positions on the aromatic ring.

In another embodiment of the present invention, wherein the product accumulation in the biotransformation medium in the high concentration may indicates a faster rate of substrate conversion and slower rate of product degradation resulting in increasing the yield of reduced carbon aromatic acid may be in the range of 70 to 80%.

In other embodiment of the present invention, wherein addition of the alkaline solution of substrate containing aromatic acid to the fermentation broth may be carried out in stepwise or continuous manner to obtain the final concentration of 1-15 g/L for aromatic acid; wherein aromatic acid is converted for 24-50 hours, most preferably within 30-40 hrs and converted liquid containing reduced carbon aromatic acid is obtained.

In another embodiment of the present invention, wherein fermentation broth may be harvested by removing cell culture by filtration or centrifugation which may be done using membrane system.

In yet another embodiment of the present invention, wherein the precipitation of reduced carbon aromatic acid can be carried out by using acid to obtain a crude product in solid form.

In still most preferred embodiment of the present invention, wherein recrystallization of crude reduced aromatic acid product may be done to obtain pure solid of reduced carbon aromatic acid which can also be used for further biotransformation to obtain other metabolites such as aldehydes and/or alcohols of commercial value or wide applications.

In the preferred embodiment, *Amycolatopsis* sp or the mutant thereof may be used to convert natural as well as synthetic aromatic acids to reduced carbon aromatic acids with wide applications.

In another embodiment of the present invention, wherein cell culture may be adapted to grow at 37-46° C. to achieve the biotransformation of aromatic acid to reduced carbon aromatic acid, which is accomplished at 37-46° C. to obtain a higher yield of the product.

In most preferred embodiment of the present invention there is provided a process for biotransformation of aromatic acid to reduced carbon aromatic acid, wherein recovery and recycling of cell culture may be carried out for subsequent biotransformation making the process continuous with multiple biotransformations using the same cell culture.

Another embodiment of the present invention, wherein cell cultures may be used used/recycled for 10-15 cycles of biotransformation without losing the organism's activity for biotransformation.

In yet most preferred embodiment of the present invention there is provided a process for biotransformation of reduced carbon aromatic acids by microbial fermentation and biotransformation of naturally occurring aromatic acids, wherein said microbe may be *Amycolatopsis mediterranei* NCIM 5008 of actinomycete species have been deposited with NCIM 5008 in the Microbial Type Culture Collection and Gene Bank ("MTCC"), CSIR-Institute of Microbial Technology, Sector 39-A, Chandigarh, 160036, India, on Mar. 24, 2017 under the accession number MTCC 25136.

Another embodiment of the present invention there is provided a process for microbial transformation of aromatic acid to reduced carbon aromatic acid, wherein the aromatic acid precursor may be first solubilised in alkaline solution and then added to the fermentation broth for 24-40 hrs at the pH of 7-9 and at a temperature in the range of 40-45° C. to convert into their reduced carbon aromatic acid.

Advantages of the technology:
1) The present invention provides accumulation of product in high concentration in the broth which simplifies the downstream processing.
2) The present invention also provides a process in which no other metabolite is formed thereby the product obtained requires only fewer steps for final isolation and purification.
3) Thus the present invention provides microbial transformation of aromatic acid to reduced carbon acid which can be used directly for subsequent biotransformation to obtain products of wide commercial value.
4) The present invention provides recycling of cell culture for biotransformation which make continuous process resulting in cost effective as it saves the media cost and the time and energy for the growth of the organism.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Example 1

Slant culture of *A. mediterranei* NCIM 5008: A culture medium containing 0.4% glucose, 0.4% yeast extract and 1% malt extract and 2.2% agar is formulated, pH 7.2. All of the contents of constituents are percentage of weight to volume i.e g/100 ml (similarly hereinafter). The culture medium is autoclaved at 121° C. for 20 minutes and made into slants after cooling. The strain *A. mediterranei* is inoculated on the slants and incubated at 43° C. for 7 days.

Example 2

Preparation of the preliminary culture: 100 ml medium containing 10 g/L Malt extract, 4 g/L glucose, 4 g/L yeast extract and 0.1 g/L magnesium sulphate is formulated, pH 7.2. Then 50 ml of the above culture medium is added to each of the 250 ml conical flasks and autoclaved at 121° C. for 20 minutes. The strain *A. mediterranei* is inoculated into the culture medium in an amount of 1-2.5%. The shake flask fermentation is performed at 43° C., 200 rpm for 48 hours. The resultant cultures are used as seed cultures for biotransformation.

Example 3

2000 ml of the production medium containing 10 g/L Malt extract, 4 g/L glucose, 4 g/L yeast extract and 0.1 g/L magnesium sulphate is formulated, pH 7.2. in a 5L fermentor. After cooling it was inoculated with 100 ml of the above seed culture medium as per Example 2. The culture conditions were 43° C., 400 rpm and 0.5 L of air per minute. After 20 hours of growth, the alkaline solution of aromatic acid substrate, ferulic acid in the concentration of 10 g/L is added and reaction continued at the same conditions. The ferulic acid solution is prepared by dissolving it in an alkaline solution and pH adjusted to 8.5 using 6M HCl before addition in the fermentor. After 40 hours of substrate addition, the fermentation is terminated and the broth is harvested by centrifugation to remove the cells and to obtain the supernatant containing reduced carbon aromatic acid, vanillic acid. The supernatant containing 7 g/L vanillic acid is obtained with 100% conversion of ferulic acid and 80% yield.

Example 4

The *Amycolatopsis* cells are grown as in example 3 for 20 hours at the same reaction conditions of 43 C, 400 rpm and 0.5L of air per minute. The suitable precursor containing aromatic acid like p-coumaric acid at a concentration of 10 g/L is dissolved in an alkaline solution and pH of the solution is adjusted to 8.5 using conc. HCl, before addition in the fermentor. This solution is then added to the broth and incubated at 43° C. for 40 hours. The final concentration of p-hydroxy benzoic acid in the broth was 6.6 g/l with 100% conversion of p-coumaric acid and final p-hydroxy benzoic acid yield of 78%.

Example 5

The *Amycolatopsis* cells are grown as in example 3 for 20 hours at the same reaction conditions of 43 C, 400 rpm and 0.5 L of air per minute. The suitable precursor containing aromatic acid like caffeic acid at a concentration of 10 g/L is dissolved in an alkaline solution and pH of the solution is adjusted to 8.5 using conc. HCl, before addition in the fermentor. This solution is then added to the broth and incubated at 43° C. for 40 hours. The final concentration of protocatechuic acid in the broth was 6 g/L with 100% conversion of p-coumaric acid and final protocatechuic acid yield of 70%.

Example 6

Resting cell biotransformation: The *Amycolatopsis* cells are grown as in example 3 in fermentor for 20 hours at the same reaction conditions of 43° C., 400 rpm and 0.5 L of air per minute. The cells were harvested by centrifugation in aseptic condition and washed twice with sterile distilled water. These cells were then directly suspended in the ferulic acid solution of the concentration of 10 g/L in the fermentor. The biotransformation was done at the following conditions: pH 8.5, 43 C, 400 rpm and 0.5L of air per minute. After complete consumption of ferulic acid, the broth was filtered using the membrane system and the cells were recycled for further biotransformation, with the addition of second dose of 10 g/L ferulic acid. This process of repeated fresh substrate addition and simultaneous product removal is done for 10 times. The vanillic acid yield obtained for each dose was 80% with final vanillic acid concentration of 7 g/L.

We claim:
1. A process for a biotransformation of aromatic acids to their reduced carbon aromatic acids comprising:
   a) culturing or growing Amycolatopsis mediterranei NCIM 5008 in a fermentor at a temperature in a range of 37-46° C. for 16-24 hours;
   b) adding an alkaline solution of substrate containing aromatic acid to a fermentation broth of step (a) to obtain the final concentration of 1-15 g/L for aromatic acid; wherein aromatic acid is converted for 24-50 hours and converted liquid containing reduced carbon aromatic acid is obtained;

c) centrifuging or filtrating the converted liquid of step (b) to obtain retentate comprising culture cells, and permeate comprising converted liquid with reduced carbon aromatic acid;

d) precipitating the converted liquid obtained from step (c) to isolate crude reduced carbon aromatic acid in solid form; and e) recrystallizing the crude reduced carbon aromatic acid from (d) to obtain pure reduced carbon aromatic acid.

2. The process as claimed in claim 1, wherein aromatic acid is selected from the group consisting of cinnamic acid, 3-methoxy-4-hydroxy cinnamic acid, 4-hydroxy cinnamic acid, 3-hydroxy cinnamic acid, caffeic acid, sinapinic acid, hydrolyzate of lignin, hydrolyzate of phenolate acid and/or aromatic acids with different substituents but similar propenic acid side chain, most preferably 3-methoxy-4-hydroxy cinnamic acid or caffeic acid or p-coumaric acid.

3. The process as claimed in claim 1, wherein reduced carbon aromatic acid is selected from the group consisting of benzoic acid, 4-hydroxy-3-methoxy benzoic acid, 4-Hydroxy benzoic acid, 3-hydroxy benzoic acid, 3,4-dihydroxy benzoic acid, 3,5-dimethoxy-4-hydroxy benzoic acid, most preferably 4-hydroxy-3-methoxy benzoic acid or protocatechuic acid or p-hydroxy benzoic acid.

4. The process as claimed in claim 1, wherein substrate concentration used for biotransformation is in the range of 1-20 g/L, more preferably 5-12 g/L.

5. The process as claimed in claim 1, wherein alkaline pH of the substrate solution is adjusted in the range of 6-9, more preferably 8-9.

6. The process as claimed in claim 1, wherein pH of the growth media is maintained in the range of 6-9, most preferably 7-8.5.

7. The process as claimed in claim 1, wherein addition of substrate solution is done in one step or step-wise manner.

8. The process as claimed in claim 1, wherein conversion of aromatic acid to their reduced carbon aromatic acid is carried out within 30-40 hours at a temperature in the range of 39 to 45° C. in a fermentation broth.

9. The process as claimed in claim 1, wherein filtration of converted liquid is carried out using membrane system.

10. The process as claimed in claim 1, wherein said culture used for biotransformation is actinomycete species.

11. The process as claimed in claim 1, wherein the aromatic acid as substrate is not used as a carbon source and/or as inducer for the biotransformation by the organism.

12. The process as claimed in claim 1, wherein said culture is reduced the propenic side chain without affecting other substituent at different positions.

13. process as claimed in claim 1, wherein yield of said reduced carbon aromatic acid is in a range of 70 to 80%.

14. The process as claimed in claim 1, wherein growth of culture by an organism is carried out on a carbon and nitrogen source.

15. The process as claimed in claim 14, wherein carbon source is selected from the group consisting of glucose, molasses, starch, sugar hydrolyzate, corn steep liquor, most preferably glucose.

16. The process as claimed in claim 15, wherein glucose used is in a concentration range from 1-40 g/L, more preferably in the range of 5-20 g/L.

17. The process as claimed in claim 14, wherein nitrogen source used is organic and/or inorganic source.

18. The process as claimed in claim 17, wherein organic source is selected from the group consisting of yeast extract, malt extract, peptone, beef extract, soy protein extract, maize gluten protein extract and/or inorganic source is selected from the group consisting of ammonium sulphate, urea, and sodium nitrate or mixture thereof.

19. The process as claimed in claim 18, wherein nitrogen source used is in a concentration of 5-50 g/L, most preferably in the range of 5-20 g/L.

20. The process as claimed in claim 1, wherein culture cells obtained from step (c) are reused/recycled for subsequent biotransformation.

21. The process as claimed in claim 20, wherein culture cells are used/recycled for 10-15 cycles of biotransformation without losing an organism's activity for biotransformation.

* * * * *